United States Patent [19]
Spencer

[11] Patent Number: 5,116,330
[45] Date of Patent: May 26, 1992

[54] SAMPLE EXTRACTION SYSTEM

[76] Inventor: R. Wilson Spencer, P.O. Box 22586, Houston, Tex. 77227

[21] Appl. No.: 656,817

[22] Filed: Feb. 15, 1991

Related U.S. Application Data

[63] Continuation-in-part of Ser. No. 435,935, Nov. 13, 1989, Pat. No. 5,003,830, which is a continuation-in-part of Ser. No. 304,815, Jan. 31, 1989, abandoned, which is a continuation of Ser. No. 55,720, May 29, 1987, Pat. No. 4,800,761.

[51] Int. Cl.⁵ .............................................. G01N 1/00
[52] U.S. Cl. .................................................. 73/863.71
[58] Field of Search ............................ 73/323–327, 73/863.61, 863.71, 863.72, 863.81–863.86, 864.34; 137/559, 208; 340/618–625

[56] References Cited

U.S. PATENT DOCUMENTS

| | | | |
|---|---|---|---|
| 258,872 | 6/1882 | Ashcroft | 340/624 |
| 506,418 | 10/1893 | Cornell | 137/559 |
| 2,199,728 | 5/1940 | Overson | 137/559 |
| 2,964,938 | 7/1957 | Fuller | 73/23 |
| 3,106,844 | 10/1963 | Sonneberg | 73/422 |
| 3,186,234 | 6/1965 | Solnick et al. | 73/422 |
| 4,338,280 | 7/1982 | Ambers et al. | 422/68 |
| 4,712,434 | 12/1987 | Herwig et al. | 73/864.63 |
| 4,755,357 | 7/1988 | Noguchi et al. | 422/103 |
| 4,862,754 | 9/1989 | Nimberger | 73/864.62 |
| 4,865,811 | 9/1989 | Newton et al. | 422/81 |
| 4,873,876 | 10/1989 | Sheridan et al. | 73/863.86 |
| 4,887,472 | 12/1989 | Jansen | 73/863.86 |
| 4,928,536 | 5/1990 | Welker | 73/863.83 |

Primary Examiner—Robert Raevis
Attorney, Agent, or Firm—Robert C. Tucker; William David Kiesel

[57] ABSTRACT

A sample extraction system is provided, comprising a sample container having an inlet and an outlet; a sample inlet line, fluidly connected at one end to a source of sample fluid and at the other end to the inlet of the sample container; a sample exit line, fluidly connected at one end to a desired outlet point and at the other end to the outlet of the sample container; a sample inlet valve, positioned in the sample inlet line; a sample exit valve, positioned in the sample exit line; a dip tube fluidly connected between the sample inlet line and the inlet of the sample container, the dip tube extending a desired distance into the sample container; a disposal line, fluidly connected to the sample inlet line; valves for selecting between inlet flow and disposal flow, adapted to select a flow path either between the source of sample fluid and the inlet of the sample container or between the disposal line and the inlet of the sample container; and a sight glass for determining the presence of gas or liquid in the disposal line, positioned in the disposal line.

5 Claims, 7 Drawing Sheets

SAMPLE EXTRACTION SYSTEM

RELATED APPLICATIONS

This is a continuation-in-part application of U.S. patent application Ser. No. 435,935, filed on Nov. 13, 1989, now U.S. Pat. No. 5,003,830, which is a continuation-in-part application of U.S. patent application Ser. No. 304,815, filed on Jan. 31, 1989, now abandoned, which is a continuation of U.S. patent application Ser. No. 55,720, now U.S. Pat. No. 4,800,761, issued on May 29, 1987, by the inventor herein, entitled "Sample Extraction System", specific mention being made to obtain the benefit of the parent applications' filing date.

BACKGROUND OF THE INVENTION

1. Field of the Invention

This invention relates generally to devices for sampling flowing fluids and, more particularly, to such devices which operate within a closed loop system and which are capable of sampling easily compressible gases.

2. Prior Art

In industrial chemical plants, as well as other industrial process operations, it is often necessary to obtain samples of fluids flowing in pipelines or various other types of vessels. Often, such fluids are of a hazardous nature, requiring that exposure of personnel to the sample be minimized or eliminated. In most applications when a sample is taken from a line flowing under pressure, samples are taken in sample cylinders. Such cylinders are well-known in the art. A typical cylinder is usually provided with a valve on either end, allowing a sample to be encased therein.

Various methods have been attempted in the art to safely force the sample into the cylinder. One method is to simply connect one end of the cylinder to the line containing the fluid, open the valve at the connected end and bleed the other end of the cylinder using the opposite valve until the cylinder is full of sample and entrained gases are displaced. This method obviously has its limitations with hazardous materials, since the bleeding step offers the possibility of exposing sampling personnel to the sample (a clear violation of current federal regulations). Other methods create a vacuum in the cylinder; elaborate means such as mercury, glycol or water displacement are also used. All of the prior art methods are prone to failure as well as exposure of sampling personnel to the sample. Further, these methods do not always result in a truly representative sample being contained in the cylinder or the sample container.

Stringent environmental regulations have resulted from an increasing concern for the safety of sampling personnel as well as exposure or discharge of hazardous materials to the atmosphere. Regulatory and safety concerns have thus severely limited sampling, resulting in elaborate and expensive containment schemes. Nevertheless, monitoring of industrial processes must still take place. Highway tank trailers, railroad cars or marine transport tanks, such as tankers or barges carrying hazardous materials such as liquified petroleum gases, ammonia, ethylene oxide or other liquids or gasses under pressure are still sampled by an operator filling a sample cylinder by any one of several means known in the art, and previously mentioned in this application. These methods expose the operator to the fluid being sampled or require the taking of elaborate safety precautions and the wearing of bulky and often cumbersome safety equipment.

In some cases where the fluid which is to be sampled is an easily compressible gas (such as propylene or butadiene), the fluid is in liquid form when sampled. However, ambient heating of the sample cylinder will result in expansion of the sample, creating hazardous vapor pressures within the sample cylinder, possibly causing the cylinder to burst. In order to accommodate safe sample cylinder transportation, a desired amount of fluid from the cylinder is released, or bled, leaving room for safe expansion (commonly referred to as "cylinder outage") of the sample fluid remaining in the cylinder. This is usually accomplished using a dip tube, which attaches to either the inlet or the outlet of the cylinder and extends a desired distance into the cylinder. In the past, the person bleeding the sample simply oriented the dip tube upward and opened the valve on the dip tube end of the sample cylinder, bleeding the sample fluid until liquid was no longer visible, indicating that the liquid level in the cylinder was below the end of the dip tube. Prior to the existence of environmental control regulations, the bleeding procedure was often simply directed into the atmosphere. Now, the bleeding step must be accomplished by transporting the sample cylinder to and bleeding waste fluids into a disposal line, such as a flare line. The presence of gas or liquid in the discharge of the sample cylinder into the disposal line can be visually monitored by placing a sight glass in line between the sample cylinder outlet and the disposal line. A serious safety problem still exists with such a system in that the sample container must be disconnected while full of dangerously expansive fluid and transported to a discharge facility, endangering sampling personnel and the environment. Further, such a disposal procedure may introduce oxygen into the disposal line, creating a serious danger of explosion.

The prior art devices have not managed to economically provide the necessary safety while maintaining the integrity of the sample and clearly demonstrate the need for the present invention.

SUMMARY OF THE INVENTION

Therefore, it is an object of this invention to provide a sample extraction system which minimizes exposure of sampling personnel to the sample.

It is another object of this invention to provide a sample extraction system which will economically obtain a representative sample and maintain maximum safety.

It is still another object of this invention to provide a sample extraction system which will not utilize significant external power to take a sample.

It is still another object of this invention to provide a sample extraction system which will return excess sample and entrained gases back into the source from which the sample came.

It is another object of this invention to provide a sample extraction system which will operate in combination with a wheeled transport tank or a marine transport tank, providing a means for readily sampling the contents of the tank.

It is another object of this invention to provide a sample extraction system which accommodates closed loop sampling of easily compressible gases, while providing in situ bleeding of the sample container to a disposal line, as well as providing a means for determining the amount of sample fluid in the sample container after bleeding the container.

It is yet a further object of this invention to provide a sample extraction system which will accomplish various combinations of the above objects.

Accordingly, a sample extraction system is provided, comprising a block fitting including an inlet, an outlet, an interior passageway providing communication between the inlet and the outlet, thereby allowing flow through the block fitting, a venturi section positioned in the interior passageway, a sample port, a sample passageway connecting the interior passageway and the sample port between the inlet and the venturi section, a reentry port, and a reentry passageway connecting the reentry port and the venturi section; a loop entry line, connected on one end to a main flow line, and on the other end to the inlet of the block fitting; a loop exit line connected on one end to the main flow line, and on the other end to the outlet of the block fitting; a sample container, having an inlet and an outlet; a sample inlet line, connected on one end to the inlet of the sample container; at least one sample inlet valve, positioned in the sample inlet line; a sample exit line, connected on one end to the outlet of the sample container, and on the other end to the reentry port; and at least one sample exit valve, positioned in the sample exit line.

When equipped with a circulating system and combined with a wheeled transport tank such as a railroad tank car or highway tank trailer or marine transport tank having a reservoir, the invention enables the user to accomplish representative emission-free sampling of such transport containers and comprises a suction line extending into the reservoir; a pump having a suction port and a discharge port, the suction port being connected to the suction line; a discharge line having a first end and a second end, connected at the first end to the discharge port; a sampling unit, for removing a sample from the discharge line, having an inlet and an outlet, the inlet being connected to the second end of the discharge line; a return line, connected on one end to the outlet of the sampling unit and terminating within the reservoir.

Variations of the invention may be used to provide closed loop sampling of easily compressible gases. One such variation comprises a sample container having an inlet and an outlet; a sample inlet line, fluidly connected at one end to a source of sample fluid and at the other end to the inlet of the sample container; a sample exit line, fluidly connected at one end to a desired outlet point and at the other end to the outlet of the sample container; a sample inlet valve, positioned in the sample inlet line; a sample exit valve, positioned in the sample exit line; a dip tube fluidly connected between the sample inlet line and the inlet of the sample container, the dip tube extending a desired distance into the sample container; a disposal line, fluidly connected to the sample inlet line; valves for selecting between inlet flow and disposal flow, adapted to select a flow path either between the source of sample fluid and the inlet of the sample container or between the disposal line and the inlet of the sample container; and a sight glass for determining the presence of gas or liquid in the disposal line, positioned in the disposal line.

DETAILED DESCRIPTION OF PREFERRED EMBODIMENTS OF THE INVENTION

Figure 1:
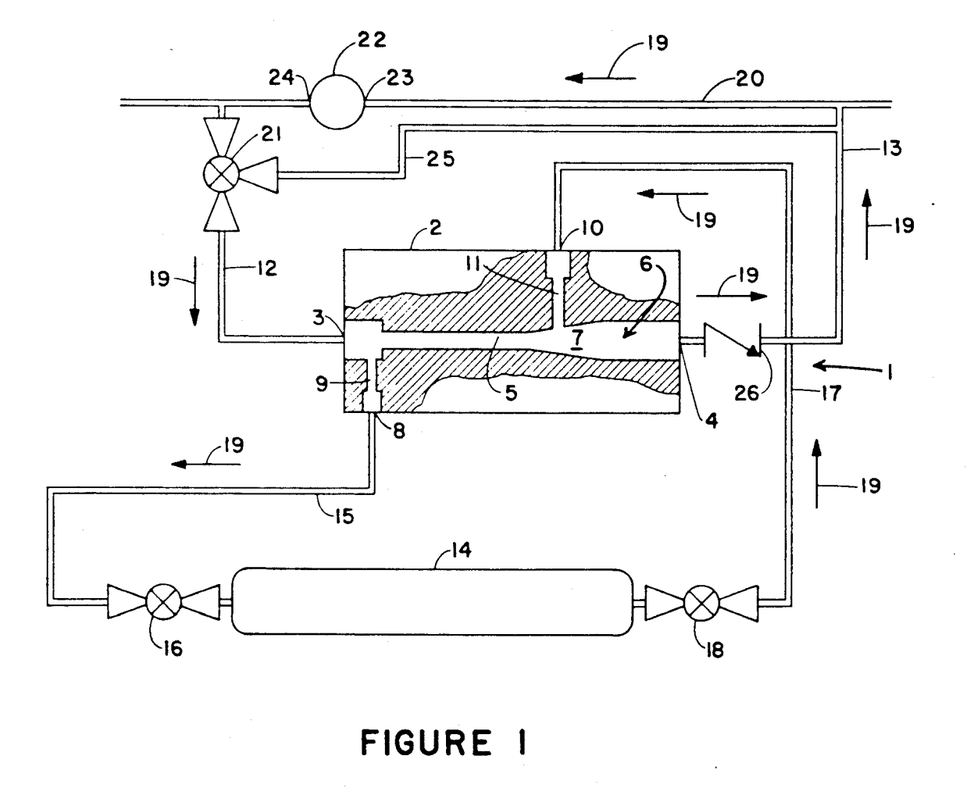
FIG. 1 is a side view of the invention with portions of the block fitting of the invention removed to sectionally reveal the interior components of the fitting.

The sample extraction system 1 is shown in FIG. 1 connected to a main flow line 20, from which a sample of flowing fluid is extracted utilizing the system 1. The system 1 utilizes the pressure differential in main flow line 20 to inject a sample of the flowing fluid into a sample container 14, usually a sample cylinder. Pressure differential may be created in a number of ways. Typically the invention may be attached to main flow line 20 on either side of an existing pressure differential caused by devices such as a pump 22 having suction port 23 and discharge port 24. Pressure differential may also be induced by devices such as an orifice plate (not shown).

As shown, the sample will flow from main flow line 20 on the discharge side of pump 22 through loop entry line 12 and into block fitting 2 at block fitting inlet 3. Flow (shown by arrows 19) is directed through block fitting interior passageway 5, exiting outlet 4 and reentering main flow line 20 through loop exit line 13, which is connected to main flow line 20 on the suction side of pump 22. Thus, a constant flow is established through block fitting 2. When sample loop valve 21 is utilized in the three-way embodiment shown, flow may be diverted through by-pass line 25 (by passing block fitting 2) and back into main flow line 20 either directly or through loop exit line 13 as shown. Check valve 26 prevents backflow into block fitting 2 through outlet 4.

Figure 4:
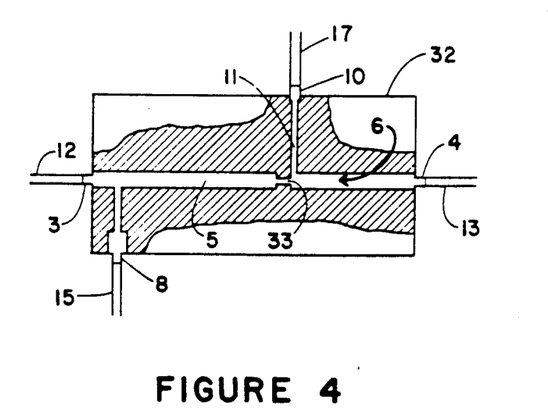
FIG. 4 is a side view of an alternate block fitting of the invention with portions removed to sectionally reveal the interior components of the fitting.

Samples are drawn from block fitting 2 utilizing the pressure differential created by pressure reducing means 6, positioned within interior passageway 5. It is preferable that pressure reducing means 6 take the form of venturi section 7 as shown. An alternate block fitting 32 is shown in FIG. 4, embodying an orifice 33 as pressure reducing means 6. As can be seen, by opening sample inlet valve 16 and sample exit valve 18, flow is established through sample passageway 9 in fitting 2, through sample port 8, sample inlet line 15, sample container 14, sample exit line 17, reentry port 10, reentry passageway 11, and into venturi section 7. In the embodiment shown in FIG. 4, reentry passageway 11 should enter interior passageway 5 just downstream of orifice 33. Valves 16 and 18 should remain open until flow is established, assuring a representative sample. Sample retention is accomplished by then closing valves 16 and 18. The sample container 14 (preferably a sample cylinder) may then be removed. Displaced gases and excess sample are thus returned to the main flow line by the system 1, resulting in little or no exposure of the sample to sampling personnel or the atmosphere.

The unique block fitting 2 (shown in partial section) is preferably unitary, and can be constructed by boring a block of material (preferably stainless steel) to form the various components described above. Thus the entire sampling process is performed by simply attaching the various lines, valves and block fitting 2 as shown to sample container 14 and main flow line 20. It should be here understood that the various lines shown may be of various lengths so as to accomplish sampling in particular locations. For example sample inlet line 15 may be very short, allowing a virtually direct connection between sample inlet valve 16 and sample port 8. Sample container 14 may then be oriented vertically with sample exit valve 18 on the top and block fitting 2 on the bottom to encourage purging of entrained gases from container 14. The rate of sampling may also be varied using valves 16, 18 and 21.

Figure 2:
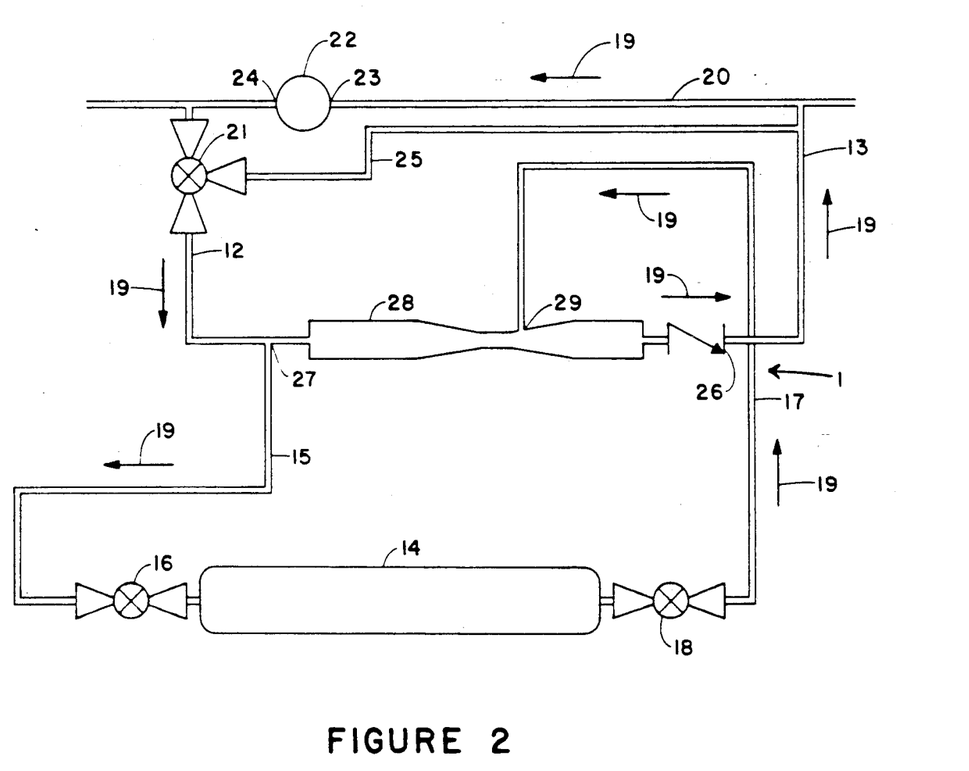
FIG. 2 is a side view of another embodiment of the invention utilizing standard fittings instead of the block fitting shown in FIG. 1.
Figure 3:
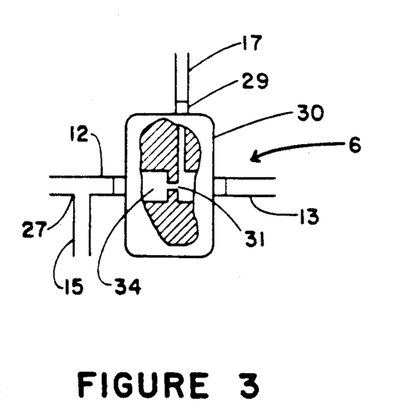
FIG. 3 is a side view of an alternate pressure reducing fitting of the invention with portions removed to sectionally reveal the interior components of the fitting.

FIG. 2 shows an alternate embodiment of the invention, wherein block fitting 2 is eliminated by inserting standard component fittings. As shown sample inlet line 15 is directly connected to loop entry line 12 by conventional means, such as tee connection 27. Just downstream from tee 27 is pressure reducing means 6, such as a venturi fitting 28 or an orifice fitting 30 (shown in FIG. 3), connected to loop entry line 12. Venturi fitting 28 (or orifice fitting 30) is provided with a reentry port 29, to which sample exit line 17 is attached. In the case of orifice fitting 30, reentry port 29 should extend to a point in orifice passageway 34 just downstream of the orifice 31. The utilization of component parts rather than block fitting 2 (similar to those shown in FIG. 2) allows for custom configurations where space restrictions are a problem. It is preferable, however, that block fitting 2 be utilized wherever possible to maximize the strength and compactness of the system 1.

Figure 5:
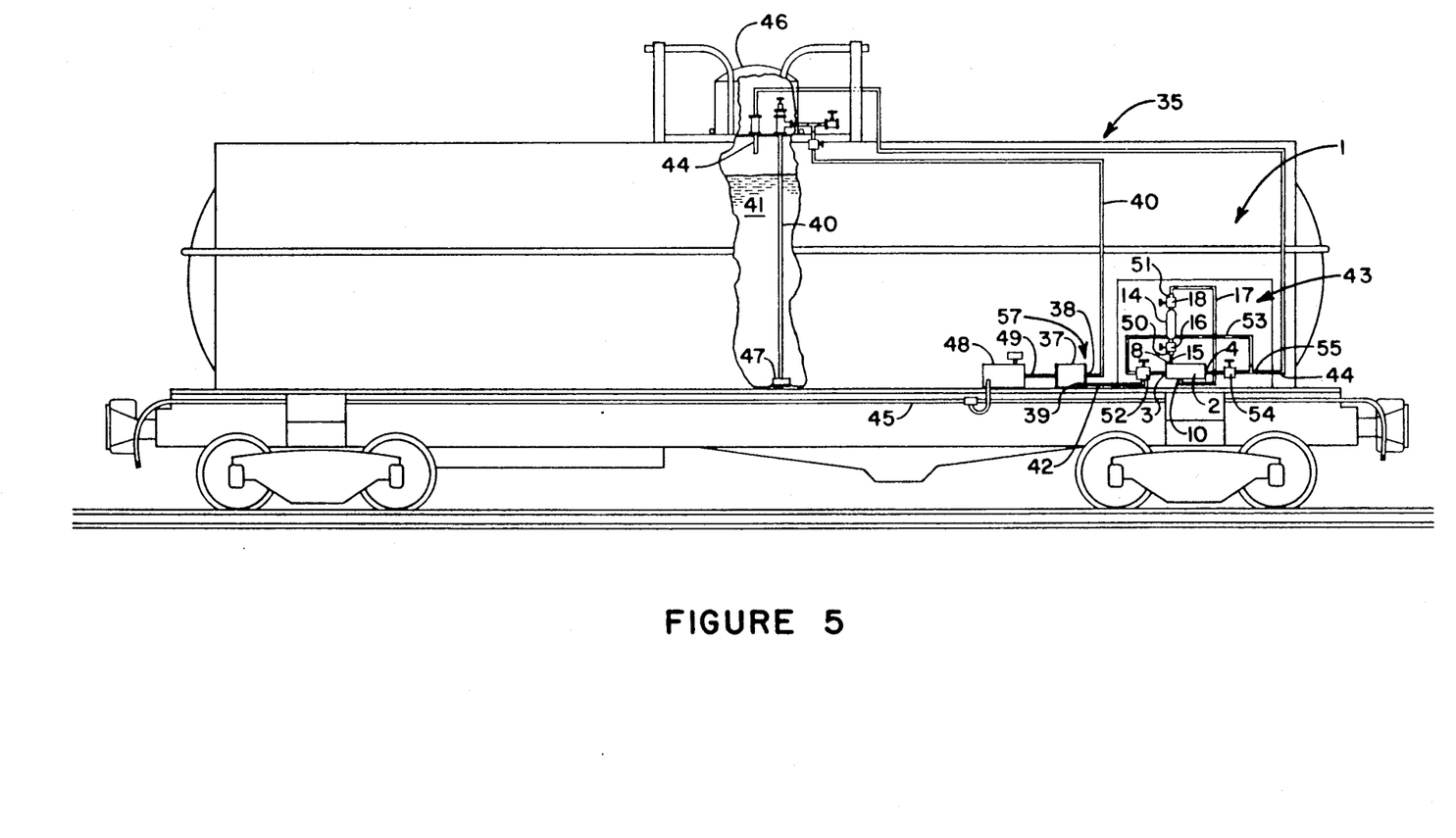
FIG. 5 is a side view of an embodiment of the invention in place on a railroad tank car.
Figure 6:
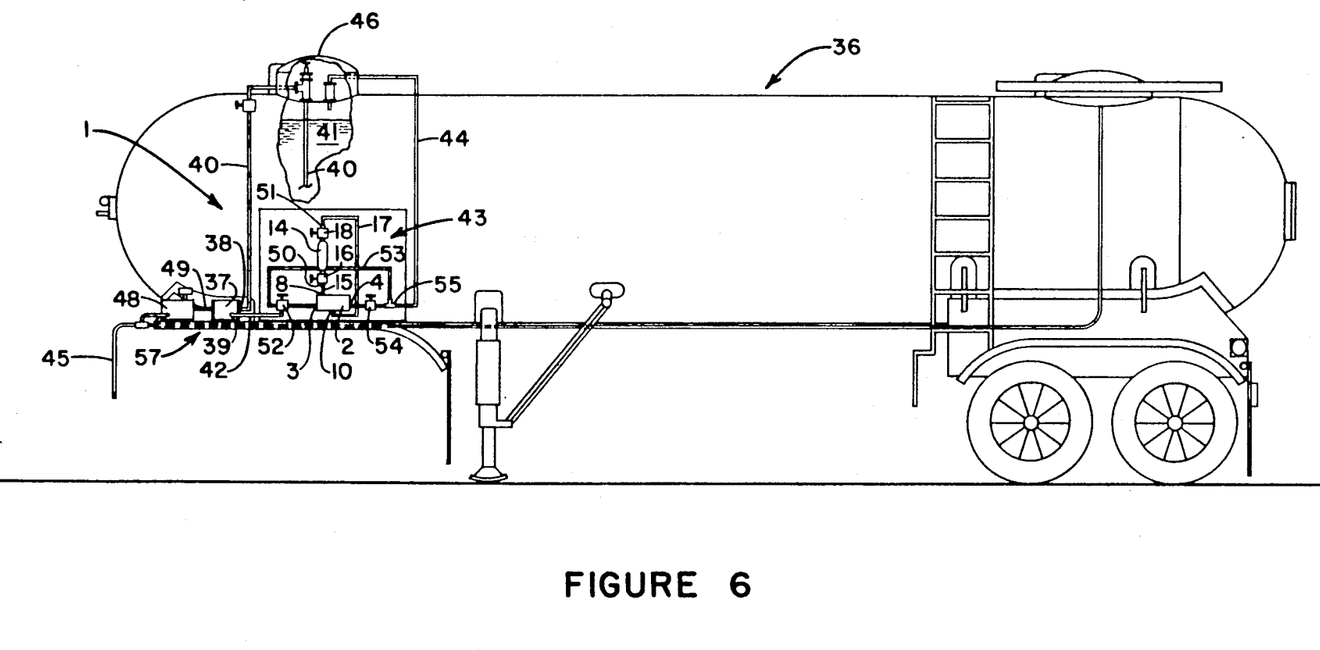
FIG. 6 is a side view of an embodiment of the invention in place on a highway tank trailer.
Figure 7:
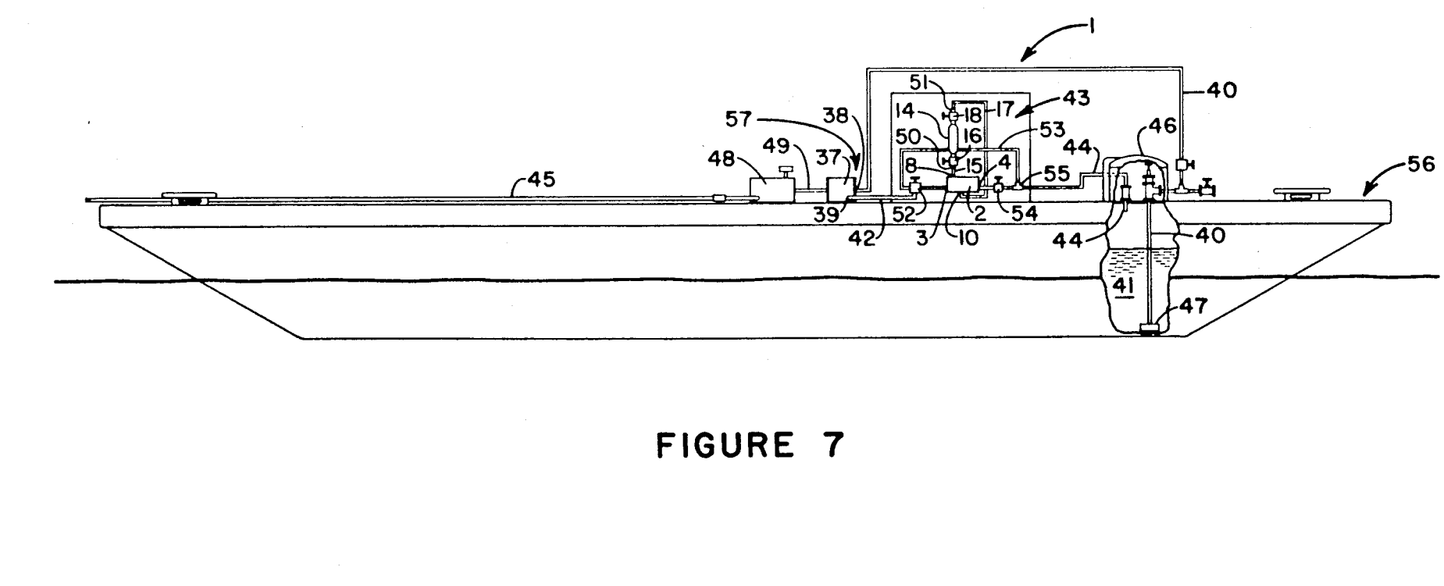
FIG. 7 is a side view of an embodiment of the invention in place on a marine barge.

A modified version of the system 1 may be used for closed loop sampling of fluids carried by wheeled transport tanks or marine transport tanks. For the purposes herein, the term "wheeled transport tanks" shall include railroad tank cars 35, such as the one shown in FIG. 5, and highway tank trailers 36, such as the one shown in FIG. 6. The term "marine transport tank" shall include marine tankers or barges, such as the one shown in FIG. 7. Each wheeled transport tank 35, 36 or marine transport tank 56 includes a reservoir 41. As shown in FIGS. 5-7, the system 1 must additionally include a circulating means 57, such as a pump 37 having a suction port 38 and a discharge port 39, for circulating fluid from reservoir 41. When the fluid in reservoir 41 is a gas, circulating means 57 could take the form of a compressor (not shown). Suction line 40 runs from within reservoir 41 to suction port 38. Discharge line 42 runs from discharge port 39 to a sampling means 43. A return line 44 runs from sampling means 43 back to reservoir 41. A sample container 14 is removably connectable to sampling means 43.

As shown in FIGS. 5-17, access to the interior of reservoir 41 may be gained through existing hatches 46. Existing valves, piping and fittings on wheeled transport tank 35, 36 may form parts of suction line 40 and return line 44. It may be desirable to furnish a filter screen 47 at the end of suction line 40, as shown. Since pressurized gas lines 45 are usually available on wheeled transport tanks 35, 36, as well as some marine transport tanks 56, it is desirable that an air motor 48 be furnished to drive circulating means 57 via a coupling, such as a magnetic coupling 49. Sampling means 43 may include block fitting 2, sample inlet line 15, sample inlet valve 16, sample exit line 17 and sample exit valve 18, or other means known in the art, such as other versions of the invention 1 more particularly described herein. First and second double seal quick disconnect couplings 50, 51, such as Snap-Tite ™ H Series double seal quick disconnects, are provided to assure quick, leak-free changes of sample containers 14. A three-way valve 52 and a two-way valve 54 may be placed in discharge line 42 and return line 44, respectively coupled to a bypass line 53 (at three-way valve 54 and tee 55) for bypassing sample means 43 while homogeneous sample flow is established.

While it is preferable that all components of the system 1 be attached to transport tanks 35, 36, 56 this is not a necessity. For example, the entire sampling system 1 could be remotely mounted so as to couple to transport tanks 35, 36, 56 only when sampling is required. However, due to governmental body sampling requirements as well as other practical considerations, it is usually preferable that the system 1 be fixedly attached to transport tanks 35, 36, 56.

Operation of the system 1 shown in FIGS. 5-7 is simple. Air motor 48 is activated, establishing flow through the system 1. If desired, three-way valve 52 is opened between discharge line 42 and bypass line 53 and valve 54 is closed to cause initial flow to pass through bypass line 53 until a homogeneous, representative sample flow is established. Valve 52 is then opened between discharge line 42 and sampling means 43 and valve 54 is opened so as to allow flow to enter sampling means 43 and return through return line 44. Sampling means 43 is operated in the normal manner, depositing a sample in sample container 14. Sample container 14 is then removed and replaced with an empty container 14. Thus, prior art sampling methods for compressed gasses and liquids under pressure and resultant contamination of the atmosphere and exposure of sampling personnel or the wearing of bulky cumbersome safety equipment are eliminated.

Figure 8:
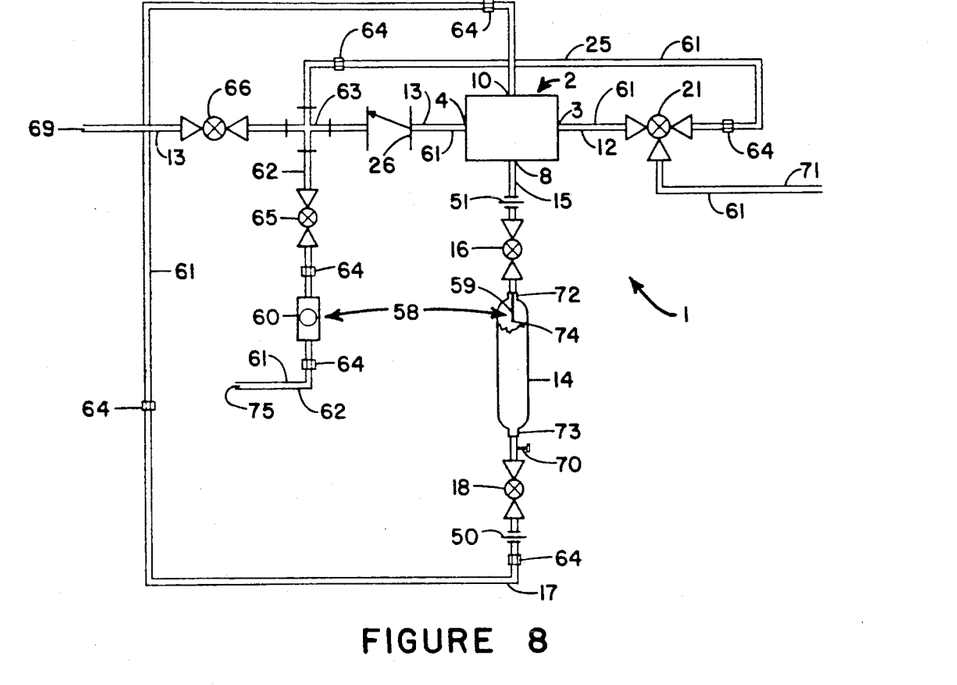
FIG. 8 is a side view of an embodiment of the invention with a portion of the wall of the sample container removed for clarity.
Figure 9:
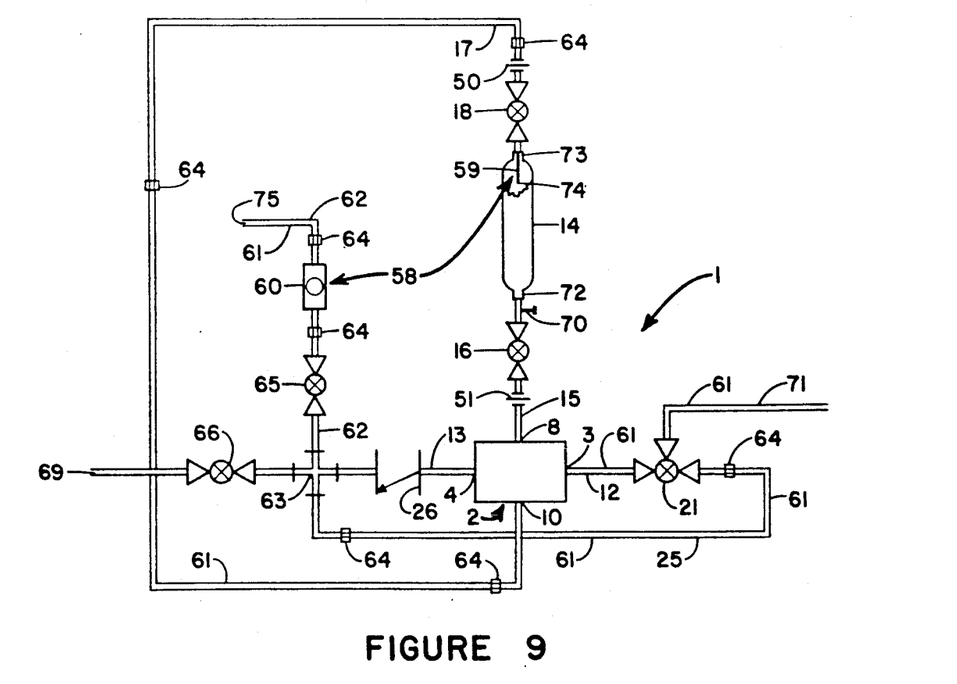
FIG. 9 is a side view of an embodiment of the invention with a portion of the wall of the sample container removed for clarity.
Figure 10:
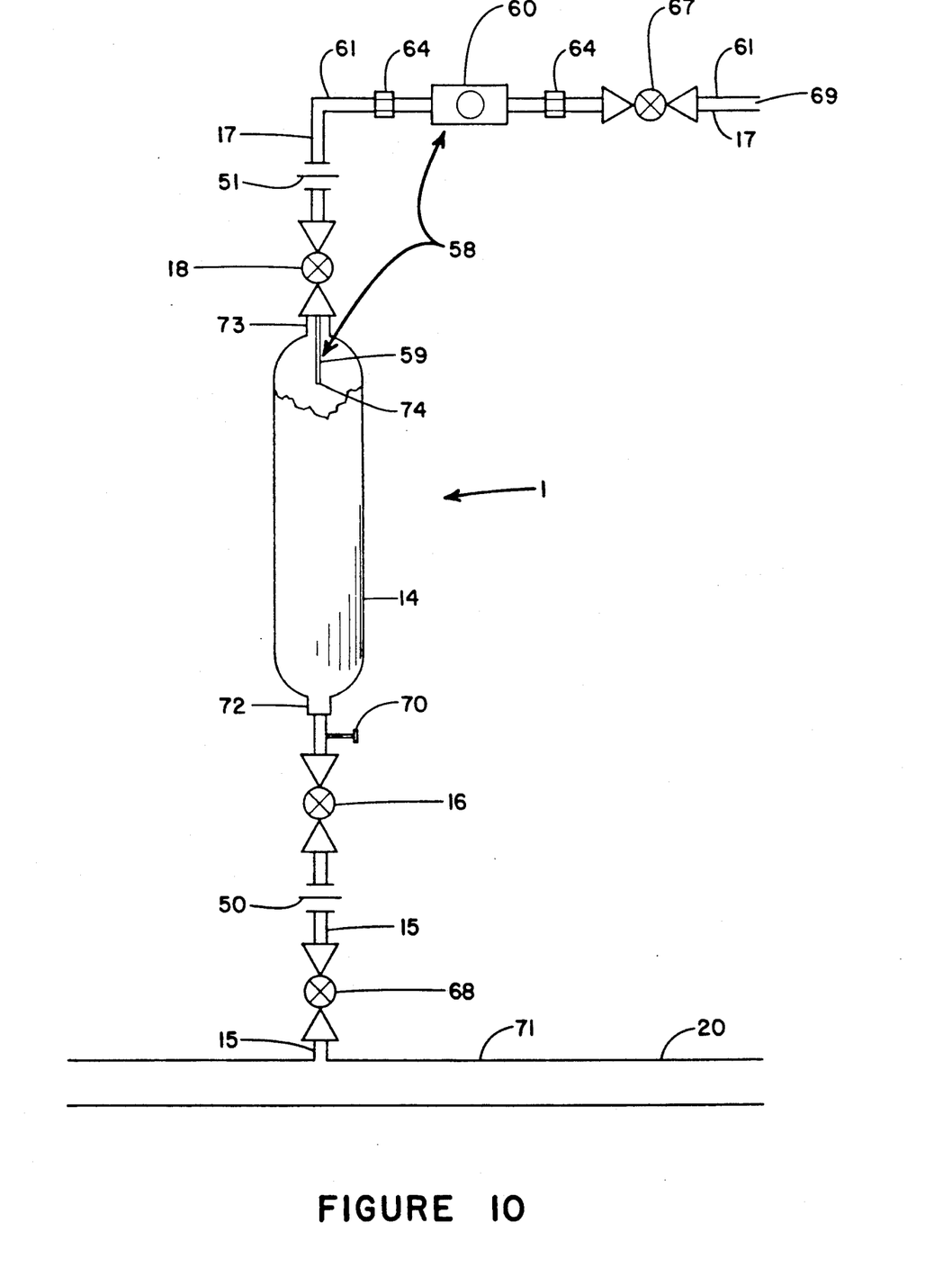
FIG. 10 is a side view of an embodiment of the invention with a portion of the wall of the sample container removed for clarity.

FIGS. 8-10 depict the invention 1 in a mode utilized for sampling easily compressible gases such as propylene or butadiene. The system allows for sampling of the fluids in a liquid state under normal operating pressures and temperatures. Once the sample is secured in sample container 14, the same system 1 used for gathering the sample is used to vent or bleed the sample container 14 for sample transportation.

This alternate embodiment is shown in its simplest form in FIG. 10. Sample inlet line 15 is fluidly connected to a source of sample fluid 71, such as a main flow line 20. Valve 68 controls flow through sample inlet line 15. Quick disconnect couplings 50,51 (described above) allow sample cylinder 14, as well as sample inlet valve 16 (connected to sample container inlet 72) and sample exit valve 18 (connected to sample container outlet 73) to be easily removed or installed. Rupture disc assembly 70 provides a relief point should the contents of sample cylinder 14 reach an unsafe pressure. Sample exit line 17 runs from sample exit valve 18 and is fluidly connected to a desired outlet point 69. Sample lines 15 and 17, as well as other lines used in the invention 1 are preferably constructed of stainless steel tubing 61. Desired outlet point 69 may be in a flare line, a reinjection point, where unused sample fluid is reinjected into main flow line 20, or other desired point. Valve 67 may be used along with valve 68 to isolate the system 1. Union fittings 64 are used to attach various pieces of tubing 61.

A means 58 is provided for determining when the quantity of sample fluid within sample cylinder 14 is reduced to a desired level. As shown in FIG. 10, means 58 preferably comprises a dip tube 59 and a sight glass 60. Dip tube 59 is fluidly connected between sample exit line 15 and outlet 73 of sample cylinder 14, extending a desired distance into sample cylinder 14, depending upon how much vapor space is desirable during the bleeding process. It is preferable that sample cylinder 14 be vertically oriented. As will be seen in FIG. 9, the system 1 will function equally well with dip tube 59 positioned in sample cylinder inlet 72, provided that inlet 72 is positioned vertically above sample cylinder outlet 73. Sight glass 60 is simply a clear fitting fluidly connected between desired outlet point 69 and dip tube 59. Observation of sight glass 60 during periods of sample disposal will allow the observer to determine whether gas or liquid is flowing through sight glass 60. In order to more easily observe the fluid flowing through sight glass 60, it may be desirable to include an orifice (not shown) or other flow restriction in exit line 17 just upstream of sight glass 60.

Operation of the embodiment shown in FIG. 10 is simple. Valves 68, 16, 18, and 67 are opened, allowing sample fluid to flow through sample cylinder 14 and out to desired outlet point 69. Where the sample fluid is an easily compressible fluid, such as propylene or butadiene, the fluid flowing through the system 1 is usually a liquid. Once a homogeneous flow is established, valves 18, 16 and 68 are closed, and sample cylinder 14 is full of sample fluid. Valve 18 is then opened while observing sight glass 60, allowing sample fluid to bleed from sample cylinder 14. When the fluid flowing through sight glass 60 is observed to be a gas, indicating that the liquid level in sample cylinder 14 has fallen below the end 74 of dip tube 59, valve 18 is closed. Valve 67 is closed, further isolating sample cylinder 14, and sample cylinder 14 is removed utilizing fittings 50 and 51 for safe transportation to a laboratory for analysis. As can be seen, dip tube 59 may extend to any desired depth into sample cylinder 14, depending upon the vapor space necessary to allow for safe expansion of sample fluid within sample cylinder 14 during transportation to the laboratory.

FIGS. 8 and 9 depict the system 1 in use with a sample loop and disposal line, in essence combining the features shown in FIGS. 1 and 10. FIG. 8 depicts the system with dip tube 59 positioned in sample container inlet 72, and FIG. 9 depicts the system with dip tube 59 positioned in sample cylinder outlet 73. As explained in greater detail above, the sampling process is initiated by opening valves 16, 18 and 66 and by opening three-way valve 21 in a position to allow flow from sample fluid source 71 to loop entry line 12, allowing sample fluid to pass through block fitting 2 to loop exit line 13 which leads to a desired outlet point 69, usually a point of reinjection into a main flow line. Since main flow line pressures are usually high enough to maintain a liquid state, venting of sample cylinder 14 is accomplished through a disposal line 62 leading to a desired disposal point 75, such as a flare line having a lower pressure.

During sampling, valve 65 is closed. As flow is established through block fitting 2, a secondary flow is established through sample inlet line 15, sample cylinder 14 and sample exit line 17, filling sample cylinder 14. A sample is then contained in sample cylinder 14 by closing valves 16 and 18. Valves 21 and 66 are also closed.

In the embodiment shown in FIG. 8, sample cylinder 14 is then bled as described previously. Valves 65 and 16 are opened, establishing flow through sample inlet line 15, block fitting 2 loop exit line 13 (through check valve 26), pipe cross fitting 63 and disposal line 62 (including valve 65 and sight glass 60). When liquid ceases to be visible in sight glass 60, valves 16 and 65 are closed and the sample cylinder 14 is disconnected and transported to the laboratory. The embodiment shown in FIG. 9 simply accomplishes the bleeding of sample cylinder 14 through sample exit valve 18 rather than sample inlet valve 16. Thus, complete sampling and bleeding of the sample cylinder 14 is accomplished without disconnecting the sample cylinder 14 from the system 1, and with waste fluids being deposited directly into disposal line 62.

As can be seen, the sample extraction system disclosed herein provides a safe and efficient means for sample extraction while preserving sample integrity. Many other embodiments of the invention will occur to those skilled in the art, and are intended to be included within the scope and spirit of the following claims.

I claim:

1. A sample extraction system, comprising:
   a. a sample container having an inlet and an outlet;
   b. a sample inlet line, fluidly connected at one end to a source of sample fluid and at the other end to said inlet of said sample container;
   c. a sample exit line, fluidly connected at one end to a desired outlet point and at the other end to said outlet of said sample container;
   d. a sample inlet valve, positioned in said sample inlet line;
   e. a sample exit valve, positioned in said sample exit line;
   f. a disposal line, fluidly connected externally of said sample container between a desired disposal point and said sample inlet line;
   g. a means for selecting between inlet flow and disposal flow, adapted to select a flow path either between said source of sample fluid and said inlet of said sample container or between said disposal line and said inlet of said sample container; and
   h. a means for determining when the quantity of sample fluid within said sample container is reduced to a desired level, fluidly connected to said inlet of said sample container, said means for determining when the quantity of sample fluid within said sample container is reduced to a desired level including:
      i. a dip tube fluidly connected between said sample inlet line and said inlet of said sample container, said dip tube extending a desired distance into said sample container; and
      ii. a sight glass, fluidly connected externally of said sample container between said desired disposal point and said dip tube.

2. A sample extraction system, comprising:
   a. a sample container having an inlet and an outlet;
   b. a sample inlet line, fluidly connected at one end to a source of sample fluid and at the other end to said inlet of said sample container;

c. a sample exit line, fluidly connected at one end to a desired outlet point and at the other end to said outlet of said sample container;
d. a sample inlet valve, positioned in said sample inlet line;
e. a sample exit valve, positioned in said sample exit line;
f. a disposal line, connected externally of said sample container between a desired disposal point and said sample inlet line;
g. a means for selecting between exit flow and disposal flow, adapted to select a flow path either between said desired outlet point and said outlet of said sample container or between said disposal line and said outlet of said sample container; and
h. a means for determining when the quantity of sample fluid within said sample container is reduced to a desired level, fluidly connected to said inlet of said sample container, said means for determining when the quantity of sample fluid within said sample container is reduced to a desired level including:
   i. a dip tube fluidly connected between said sample inlet line and said inlet of said sample container, said dip tube extending a desired distance into said sample container; and
   ii. a sight glass, fluidly connected externally of said sample container between said desired disposal point and said dip tube.

3. A sample extraction system, comprising:
a. a sample container having an inlet and an outlet;
b. a sample inlet line, fluidly connected at one end to a source of sample fluid and at the other end to said inlet of said sample container;
c. a sample exit line, fluidly connected at one end to a desired outlet point and at the other end to said outlet of said closed sample container;
d. a sample inlet valve, positioned in said sample inlet line;
e. a sample exit valve, positioned in said sample exit line; and
f. a means for determining when the quantity of sample fluid within said sample container is reduced to a desired level, fluidly connected to said inlet of said sample container, said means for determining when the quantity of sample fluid within said sample container is reduced to a desired level including:
   i. a dip tube fluidly connected between said sample inlet line and said inlet of said sample container, said dip tube extending a desired distance into said sample container; and
   ii. a sight glass, fluidly connected externally of said sample container between said desired outlet point and said dip tube.

4. A sample extraction system, comprising:

a. a block fitting, including:
   i. an inlet;
   ii. an outlet;
   iii. an interior passageway, providing communication between said inlet and said outlet thereby allowing fluid to flow through said block fitting;
   iv. a pressure reducing means, for causing a pressure drop within said interior passageway, positioned within said interior passageway;
   v. a sample port;
   vi. a sample passageway, connecting said interior passageway and said sample port between said inlet and said pressure reducing means;
   vii. a re-entry port; and
   viii. a re-entry passageway, connecting said re-entry port and said pressure reducing means;
b. a loop entry line, fluidly connected at a first point to a source of sample fluid, and on the other end to said inlet of said block fitting;
c. a loop exit line, fluidly connected on one end to a desired outlet point, and on the other end to said outlet of said block fitting;
d. a sample container, having an inlet and an outlet;
e. a sample inlet line, fluidly connected on one end to said sample port, and on the other end to said inlet of said sample container;
f. at least one sample inlet valve, positioned in said sample inlet line;
g. a sample exit line, fluidly connected on one end to said outlet of said sample container, and on the other end to said re-entry port;
h. at least one sample exit valve, positioned in said sample exit line;
i. a disposal line, fluidly connected between a desired disposal point and said sample container;
j. a means for selecting between inlet flow and disposal flow, adapted to select a flow path either between said sample container and said desired outlet point or between said sample container and said disposal line; and
k. a means for determining when the quantity of sample fluid within said sample container is reduced to a desired level, fluidly connected to said sample container.

5. A sample extraction system according to claim 4, wherein said means for determining when the quantity of sample fluid within said sample container is reduced to a desired level includes:
   i. a dip tube fluidly connected either between said sample inlet line and said inlet of said sample container or between said sample exit line and said outlet of said sample container, said dip tube extending a desired distance into said sample container; and
   ii. a sight glass, fluidly connected between said desired disposal point and said dip tube.

* * * * *